US009555150B2

(12) United States Patent
Yhlen et al.

(10) Patent No.: US 9,555,150 B2
(45) Date of Patent: Jan. 31, 2017

(54) ABSORBENT ARTICLES COMPRISING AN ORGANIC ZINC SALT AND AN ANTI-BACTERIAL AGENT OR ALKALI METAL CHLORIDE OR ALKALINE EARTH METAL CHLORIDE

(75) Inventors: Birgitta Yhlen, Mölnlycke (SE); Catarina Linnér, Lindome (SE); Jan Petrusson, Göteborg (SE); Jan Wästlund-Karlsson, Mölndal (SE)

(73) Assignee: SCA HYGIENE PRODUCTS AB, Gothenburg (SE)

( * ) Notice: Subject to any disclaimer, the term of this patent is extended or adjusted under 35 U.S.C. 154(b) by 2043 days.

(21) Appl. No.: 12/514,911

(22) PCT Filed: Nov. 17, 2006

(86) PCT No.: PCT/EP2006/011067
§ 371 (c)(1),
(2), (4) Date: May 14, 2009

(87) PCT Pub. No.: WO2008/058564
PCT Pub. Date: May 22, 2008

(65) Prior Publication Data
US 2010/0047303 A1 Feb. 25, 2010

(51) Int. Cl.
*A61F 13/15* (2006.01)
*A61L 15/46* (2006.01)
*A61L 15/18* (2006.01)
*A61F 13/511* (2006.01)

(52) U.S. Cl.
CPC ........... *A61L 15/46* (2013.01); *A61L 15/18* (2013.01); *A61F 13/51113* (2013.01); *A61F 2013/51117* (2013.01); *A61L 2300/102* (2013.01); *A61L 2300/21* (2013.01); *A61L 2300/404* (2013.01); *A61L 2300/45* (2013.01)

(58) Field of Classification Search
CPC ............... A61F 13/51113; A61F 2013/51117
USPC .... 604/375, 359, 360, 367; 442/59, 96, 118, 442/123; 424/76.1–76.4
See application file for complete search history.

(56) References Cited

U.S. PATENT DOCUMENTS

| | | | |
|---|---|---|---|
| 2,693,439 A | 11/1954 | Blanchard et al. | |
| 4,430,381 A | 2/1984 | Harvey | |
| 4,959,060 A | 9/1990 | Shimomura | |
| 5,558,655 A | 9/1996 | Jezzi et al. | |
| 5,721,295 A | 2/1998 | Bruggemann et al. | |
| 5,847,031 A | 12/1998 | Klimmek et al. | |
| 5,882,638 A | 3/1999 | Dodd et al. | |
| 6,015,547 A | 1/2000 | Yam | |
| 6,153,209 A | 11/2000 | Vega et al. | |
| 6,217,890 B1 | 4/2001 | Paul et al. | |
| 6,417,425 B1 | 7/2002 | Whitmore et al. | |
| 6,462,252 B1 | 10/2002 | Runeman et al. | |
| 6,492,574 B1 | 12/2002 | Chen et al. | |
| 6,503,526 B1 | 1/2003 | Krzysik et al. | |
| 6,852,904 B2 | 2/2005 | Sun et al. | |
| 6,967,025 B2 | 11/2005 | Di Cintio et al. | |
| 7,005,557 B2 | 2/2006 | Klofta et al. | |
| 7,265,257 B2 | 9/2007 | Baldwin et al. | |
| 7,687,450 B2 | 3/2010 | Li et al. | |
| 2002/0128621 A1 | 9/2002 | Kruchoski et al. | |
| 2003/0077307 A1 | 4/2003 | Klofta et al. | |
| 2003/0135172 A1 | 7/2003 | Whitmore et al. | |
| 2003/0144637 A1 | 7/2003 | Sun et al. | |
| 2004/0014226 A1 | 1/2004 | Schrof et al. | |
| 2004/0024374 A1 | 2/2004 | Hjorth et al. | |
| 2004/0180093 A1 | 9/2004 | Burton et al. | |
| 2004/0213892 A1 | 10/2004 | Jonas et al. | |
| 2005/0005869 A1 | 1/2005 | Fritter et al. | |
| 2005/0101927 A1 | 5/2005 | Joseph et al. | |
| 2006/0036222 A1 | 2/2006 | Cohen et al. | |
| 2006/0036223 A1 | 2/2006 | Baldwin et al. | |
| 2006/0064068 A1 | 3/2006 | Klofta et al. | |
| 2006/0122569 A1 | 6/2006 | Drevik et al. | |
| 2009/0124989 A1 | 5/2009 | Wastlund-Karlsson et al. | |
| 2011/0015596 A1 | 1/2011 | Wastlund-Karlsson et al. | |
| 2011/0054430 A1 | 3/2011 | Wastlund-Karlsson et al. | |

FOREIGN PATENT DOCUMENTS

| | | |
|---|---|---|
| DE | 1792074 A1 | 10/1971 |
| DE | 2548344 A1 | 11/1976 |
| DE | 29 00 263 A1 | 7/1980 |
| DE | 38 08 114 A1 | 9/1989 |
| DE | 199 29 106 A1 | 12/2000 |
| DE | 200 15 738 U1 | 1/2001 |
| DE | 199 37 871 A1 | 2/2001 |
| DE | 102 56 569 A1 | 4/2003 |

(Continued)

OTHER PUBLICATIONS

Official Action issued on Jul. 22, 2011 in corresponding U.S. Appl. No. 12/514,954.
Office Action issued on Mar. 9, 2011, in copending U.S. Appl. No. 12/084,880.
Wastlund-Karlsson et al., U.S. Appl. No. 12/084,880, "Absorbent Articles Comprising Acidic Superabsorber and an Organic Zinc Salt", filed May 12, 2008.
Wastlund-Karlsson et al., U.S. Appl. No. 12/514,942, "Absorbent Articles Comprising Acidic Cellulosic Fibers and an Organic Zinc Salt", filed May 14, 2009.
Wastlund-Karlssson, U.S. Appl. No. 12/514,954, "Absorbent Articles Comprising a Peroxy Compound and an Organic Zinc Salt", filed May 14, 2009.

(Continued)

*Primary Examiner* — Jacqueline Stephens
(74) *Attorney, Agent, or Firm* — Buchanan Ingersoll & Rooney PC

(57) ABSTRACT

An absorbent article, such as a diaper, panty diaper, sanitary napkin or incontinence device includes a topsheet, a backsheet and an absorbent core enclosed between the topsheet and the backsheet. The absorbent core includes an antibacterial agent or an alkali metal or alkaline earth metal chloride in combination with an organic zinc salt, in particular, zinc ricinoleate. The combination of antibacterial or (earth) alkali metal chloride and organic zinc salt exerts a synergetic effect in the suppression of malodours, such as ammonia.

11 Claims, No Drawings

(56) References Cited

FOREIGN PATENT DOCUMENTS

| | | |
|---|---|---|
| EP | 0 165 074 A2 | 12/1985 |
| EP | 0 311 344 A2 | 10/1988 |
| EP | 0 366 869 A2 | 5/1990 |
| EP | 0 564 307 A1 | 10/1993 |
| EP | 0 631 768 A1 | 1/1995 |
| EP | 0 640 330 A1 | 3/1995 |
| EP | 0 878 481 A1 | 11/1998 |
| EP | 1 034 804 A1 | 9/2000 |
| EP | 1 532 990 A1 | 5/2005 |
| FI | 1 217 978 A1 | 7/2002 |
| GB | 1 282 889 | 7/1972 |
| GB | 1 477 571 | 6/1977 |
| GB | 2 084 872 | 4/1982 |
| GB | 2 326 348 A | 12/1998 |
| JP | 62-235364 A | 10/1987 |
| JP | 2-1265 A | 1/1990 |
| JP | 10-328284 A | 12/1998 |
| JP | 11-263850 A | 9/1999 |
| JP | 2000-505692 | 5/2000 |
| JP | 2002-508222 | 3/2002 |
| JP | 2002-511005 A | 4/2002 |
| JP | 2003-510165 A | 3/2003 |
| JP | 2003-520105 | 7/2003 |
| JP | 2003-521267 | 7/2003 |
| JP | 2003-230623 | 8/2003 |
| JP | 2004-285202 A | 10/2004 |
| JP | 2005-528971 | 9/2005 |
| JP | 2009-515622 | 4/2009 |
| JP | 2010-509953 | 4/2010 |
| SE | 9502588 A | 1/1997 |
| SE | 9801951 A | 9/1999 |
| SE | 9804390 A | 6/2000 |
| WO | WO 92/13577 A1 | 8/1992 |
| WO | WO 95/01147 A1 | 1/1995 |
| WO | WO 97/02846 A1 | 1/1997 |
| WO | WO 97/45013 A1 | 12/1997 |
| WO | WO 97/46188 A1 | 12/1997 |
| WO | WO 97/46190 A1 | 12/1997 |
| WO | WO 97/46192 A1 | 12/1997 |
| WO | WO 97/46193 A1 | 12/1997 |
| WO | WO 97/46195 A1 | 12/1997 |
| WO | WO 97/46196 A1 | 12/1997 |
| WO | WO 98/17239 A1 | 4/1998 |
| WO | WO 98/26808 | 6/1998 |
| WO | WO 98/26808 A2 | 6/1998 |
| WO | WO 98/57677 A1 | 12/1998 |
| WO | WO 99/00090 A1 | 1/1999 |
| WO | WO 99/17813 A1 | 4/1999 |
| WO | WO 99/30753 | 6/1999 |
| WO | WO 99/30753 A1 | 6/1999 |
| WO | WO 99/45099 A1 | 9/1999 |
| WO | WO 00/00110 | 1/2000 |
| WO | WO 00/10500 A1 | 3/2000 |
| WO | WO 00/35502 A1 | 6/2000 |
| WO | WO 00/35503 A1 | 6/2000 |
| WO | WO 00/35505 A1 | 6/2000 |
| WO | WO 00/69481 A1 | 11/2000 |
| WO | WO 01/15649 A1 | 3/2001 |
| WO | WO 01/24756 A1 | 4/2001 |
| WO | WO 03/051250 | 6/2003 |
| WO | WO 03/051410 A1 | 6/2003 |
| WO | WO 03/092568 A1 | 11/2003 |
| WO | WO 03/105916 | 12/2003 |
| WO | WO 2005/035013 A1 | 4/2005 |
| WO | WO 2005/063310 A1 | 7/2005 |
| WO | WO 2005/081811 A2 | 9/2005 |
| WO | WO 2007/057043 A1 | 5/2007 |
| WO | WO 2007/057211 A1 | 5/2007 |
| WO | WO 2007/120617 A2 | 10/2007 |

OTHER PUBLICATIONS

International Search Report issued on Apr. 13, 2007 in International Patent Application No. PCT/EP2006/011073 in related U.S. Appl. No. 12/084,880.
Zekorn, R., "Zinc Ricinoleate," Cosmetics & Toiletries, Wheaton, IL vol. 112, 1997, pp. 37-40.
Böhmer et al., "Development and Analytic of Odor Absorber," Tenside, Surfactants, Detergents; Carl Hanser Verlag, Munchen DE, vol. 41, No. 6, 2004, pp. 282-286.
English language translation of an Office Action issued on Dec. 6, 2011 by the Japanese Patent Office in corresponding Japanese Patent Application No. 2009-536610.
International Preliminary Report on Patentability and Written Opinion issued in International Patent Application No. PCT/EP2006/011073, May 20, 2008, The International Bureau of WIPO, Geneva, CH (6 pages).
Official Action dated Sep. 15, 2010 issued in Russian Application No. 2009123021 (4 pages), and English-language translation thereof (2 pages).
Official Action dated Feb. 28, 2011, issued in Chinese Patent Application No. 200680051348.7 (4 pages), and English-language translation thereof (3 pages).
Official Action issued on Jul. 22, 2011 in U.S. Appl. No. 12/514,954 (8 pages).
Official Action issued on Sep. 9, 2011 in U.S. Appl. No/ 12/514,942 (12 pages).
Official Action issued on Oct. 28, 2011 in U.S. Appl. No. 12/514,954 (14 pages).
Office Action dated May 15, 2012 issued by the Japanese Patent Office in JP 2009-536609 (2 pages), and English-language translation thereof (3 pages).
Notice of Allowance dated May 15, 2012 issued by the Japanese Patent Office in JP 2008-540525 (4 pages).
Notice of Allowance issued Jun. 1, 2012 in U.S. Appl. No. 12/514,942 (9 pages).
English language translation of an Official Action issued on Aug. 30, 2011 by the Japanese Patent Office in Japanese Patent Application No. 2009-536609.
Official Action issued on Aug. 30, 2011 by the Japanese Patent Office in Japanese Patent Application No. 2008-540525, and English language translation of the Official Action.
Notice of Opposition filed May 19, 2011 in corresponding EP Application No. 2083873.

ABSORBENT ARTICLES COMPRISING AN ORGANIC ZINC SALT AND AN ANTI-BACTERIAL AGENT OR ALKALI METAL CHLORIDE OR ALKALINE EARTH METAL CHLORIDE

The present invention relates to an absorbent article such as a diaper, panty diaper, sanitary napkin or incontinence device comprising an effective odour control system. The present invention relates in particular to such absorbent articles wherein an organic zinc salt such a zinc ricinoleate and an anti-bacterial agent or alkali metal chloride or alkaline earth metal chloride interact to reduce malodours such as ammonia.

TECHNICAL BACKGROUND

One important area of development in the area of absorbent articles of the above-mentioned type is the control of odourous compounds forming typically after the release of body fluids, especially over a longer period of time. These compounds include fatty acids, ammonia, amines, sulphur-containing compounds and ketones and aldehydes. They are present as natural ingredients of body fluids or result from degradation processes of natural ingredients such as urea, which are frequently assisted by microorganisms occurring in the urogenital flora.

Various approaches exist to suppress the formation of unpleasant odours in absorbent articles. WO 97/46188, WO 97/46190, WO 97/46192, WO 97/46193, WO 97/46195 and WO 97/46196 teach for instance the incorporation of odour inhibiting additives or deodorants such as zeolites and silica. The absorption of bodily liquids reduces however the odour inhibiting capacity of zeolites as soon as these become saturated with water, as mentioned for instance in WO 98/17239.

A second approach involves the addition of lactobacilli with the intention of inhibiting malodour-forming bacteria in the product. The incorporation of lactobacilli and their favourable effect are disclosed for instance in SE 9703669-3, SE 9502588-8, WO 92/13577, SE 9801951-6 and SE 9804390-4.

Another approach is the use of partially neutralized super-absorbent materials (acidic superabsorbent materials) (see WO 98/57677, WO 00/35503 and WO 00/35505).

Therefore, an ongoing demand exists in the art for effective odour-control systems in absorbent articles. In particular, it would be desirable to provide an odour-control system which achieves efficient odour reduction while maintaining the bacterial flora in the urogenital region.

US 2006/0036223 and US 2006/0036222 disclose absorbent articles comprising a bodily exudate modifying agent, a skin care formulation, and a bodily exudate modifying agent neutralizer. The latter may be an enzyme inhibitor which can be selected from a large group of compounds including zinc salts of both saturated and unsaturated mono-carboxylic acids. Optionally, the skin care formulation comprises a further ingredient selected from the group comprising amongst many other members preservatives, antimicrobial actives and antifungal actives. US 2006/0036223 and US 2006/0036222 aim at reducing the viscosity of bodily exudates to facilitate absorption of the exudates into the absorbent article. Odour reduction is not an issue.

EP-A-165 074 describes a hydrophilic polymer material, e.g. for the manufacture of sanitary napkins and diapers. The hydrophilic polymer material can be produced by a process during which a specific hydrogel is dried and may be contacted with an aqueous solution. Apart from electrolytes, nutrients, physiologically active polypeptides and proteins, the aqueous solution may also contain antibacterial agents. Moreover, zinc ions may be incorporated into the hydrogel, e.g. in the form of zinc sulphate or a salt of an acidic amino acid. Zinc ions are stated as having a beneficial effect on cell growth. Odour reduction is not addressed in the reference.

The bacteriostatic, bactericidal and antifungal compositions of EP-A-0 366 869 comprise lysozyme, a mineral component and an immunomodulating agent. The mineral component, which is stated as enhancing the mycobactericidal effect of lysozyme, may comprise zinc and/or iodine (Claim 5). Zinc can be provided as zinc sulfate, zinc oxide, zinc gluconate and other salts and compounds of zinc. The immunomodulating agent contained in the composition may be selected from, among many others, benzoic acid.

U.S. Pat. Nos. 5,721,295 and 5,847,031 relate to absorbent polymer compositions comprising an ionic or covalent cross-linking agent. The ionic cross-linking agent may be a metallic compound selected from the group consisting of water-soluble magnesium, calcium, aluminum, zirconium, iron and zinc compounds (cf. Claims 6 and 21 of D8a; and Claims 6 and 19 of D8b). The zinc compounds may be the salts of inorganic acids or carboxylic acids. A huge many of suitable covalent cross-linking agents is mentioned in the reference, amongst those citric acid. U.S. Pat. Nos. 5,721,295 and 5,847,031 further describe an active substance-containing composition comprising the absorbent polymer composition and at least one active substance, which may be selected from the group consisting of drugs, pesticides, bactericides and perfumes. The focus of the references is on biodegradability, and odour reduction is not an issue.

U.S. Pat. No. 6,015,547 relates to a storage clarity-stable aqueous or aqueous/alcoholic solution of zinc ions in the presence of at least one of bicarbonate and carbonate ions. The solution comprises a zinc salt of a first anion. Optionally, the solution may contain antibacterial agents. The gist of the patent is on combining zinc ion containing compounds and bicarbonate and/or carbonate ion containing compounds each of which is in solution, i.e. without liberation of carbon dioxide and without the formation of insoluble basic salts of zinc and carbonate.

The articles for applying a skin care composition to the skin in accordance with U.S. Pat. No. 6,153,209 may comprise a skin care agent which, amongst a large number of compounds, may be zinc acetate. Antibacterial actives are mentioned in a long list of further ingredients. However, the reference does not suggest any effect in terms of odour reduction by using a combination of an organic zinc salt, such as zinc acetate and a preservative.

U.S. Pat. No. 7,005,557; US 2003/0077307 and US 2006/0064068 relate to articles, in particular disposable absorbent articles having a film-forming composition comprising a viscosity enhancing agent, and optionally anti-microbials (selected from a lengthy group). The documents provide a very long list of viscosity enhancing agents including metal ester complexes of aluminum, magnesium, or zinc with stearates, behenates, palmitates or laureates. The object of these documents is not the reduction of odour but the formation of a protective barrier against fluids, body exudates and other irritants.

The highly swellable absorption medium of US 2004/0213892 comprises at least one Lewis acid as a coating agent. A large number of suitable Lewis acids is provided, amongst those benzoic acid, citric acid and water-soluble acetates, formates, oxalates or lactates of inter alia zinc. However, the document fails to disclose a preservative in combination with an organic zinc salt. Moreover, the object of US 2004/0213892 is on a reduced caking tendency in a moist environment and/or at high temperatures, whereas odour reduction is not an issue.

US 2005/0101927 is concerned with moisturizing and lubricating compositions which may be used on absorbent products. The absorbent products comprise an immobilizing agent. Many compounds, including zinc stearate, are stated as being suitable as the immobilizing agent. While the optional addition of preservatives is envisaged, odour reduction is not an issue.

WO 99/00090 relates to a faecal management device which comprises a specific bag comprising a moisture vapour permeable wall material. According to a specific embodiment, the wall material further comprises an odour control agent. Many odour control agents are exemplified, amongst those zinc ricinoleate and, as a different type of odour control agents, antimicrobics such as benzoic and sorbic acid. However, WO 99/00090 fails to disclose a preservative and organic zinc salt in combination for achieving malodour reduction. In particular, the function of zinc ricinoleate as an ammonia absorber is not addressed.

WO 99/30753 is concerned with odour control particles for use in absorbent articles. The odour control particles comprise an effective amount of a liquid activated particle separating means. There are two kinds of these separating means, namely physical and chemical ones. Sodium chloride (NaCl) is given as an example of a physical separating means. Citric acid is exemplified as a chemical separating means. The odour control particles for absorbent particles comprise odour control active materials, amongst those zinc cations. Any other known odour control active is referred to as being likewise suitable for combating malodours. No organic zinc salt is mentioned in WO 99/30753.

DE 10256569 A1 relates to water-absorbing, crosslinked, acid group-containing polymers in the form of mainly open-cell foam comprising at least one odour control agent selected from compounds with an anhydride group, compounds with an acidic group, cyclodextranes, bactericides and surfactants with an HLB value of less than 12. One example of bactericidal compounds are zinc compounds such as zinc chloride. However, no organic zinc salt is mentioned in this reference.

From other technical areas it is further known that organic zinc salts of unsaturated hydroxylated fatty acids such as zinc ricinoleate are deodorizing active ingredients (see for instance DE-A-1792074, DE-A-2548344 and DE-A-3808114).

As will be appreciated from the above, the prior art is not aware of the favorable, in particular synergistic effects of using an antibacterial or alkali metal chloride in combination with an organic zinc salt.

It is one technical object of the present invention to overcome deficiencies discussed above in connection with the prior art.

It is one further technical object to provide an absorbent article having an efficient odour control system.

It is one further technical object of the present invention to considerably reduce or eliminate ammonia formation in absorbent articles.

Further objects will become apparent from the following description of the invention.

BRIEF DESCRIPTION OF THE INVENTION

The present invention relates to an absorbent article, such as a diaper, panty diaper, panty liner, sanitary napkin or incontinence device comprising a topsheet, a backsheet and an absorbent core enclosed between said topsheet and said backsheet, wherein said absorbent core comprises
(i) an anti-bacterial agent or, in an amount of at least 0.01 g/g of said absorbent core, at least one alkali metal or alkaline earth metal chloride, and
(ii) an organic zinc salt.

The present inventors have found that anti-bacterial agents and organic zinc salt, such as zinc ricinoleate interact favorably in the suppression of unpleasant odours.

The same observation was made with alkali metal or alkaline earth metal chlorides such as NaCl. Although these normally are not referred to as "antibacterial" they control bacterial growth when used in higher concentration.

Without wishing to be bound by theory, the mechanism underlying the odour reduction of the present invention is assumed to be as follows. It was found that the ammonia which produces the malodour in absorbent products, such as incontinence products is formed in the following way:

Bacteria+Urea→NH$_3$

In the present invention, the antibacterial, e.g. the benzoic acid, or alkali metal chloride has the function of suppressing bacterial growth while the organic zinc salt, e.g. the zinc ricinoleate removes the ammonia (NH$_3$) actually formed.

The aim of the present invention is to develop an absorbent article where the amount of unwanted bacteria, such as ammonia-producing bacteria does not increase during use.

DETAILED DESCRIPTION OF THE INVENTION

Throughout the specification and claims, the use of "comprising" is intended to cover also the more restricting meanings "essentially consisting of" and "consisting".

As "absorbent article" we understand articles capable of absorbing body fluids such as urine, watery feces, female secretion or menstrual fluids. These absorbent articles include, but are not limited to diapers, panty diapers, panty liners, sanitary napkins or incontinence device (as used for instance for adults).

Such absorbent articles have a liquid-pervious topsheet, which during use is facing the wearer's body. They further comprise a (preferably liquid-impervious) backsheet, for instance a plastic film, a plastic-coated nonwoven or a hydrophobic nonwoven and an absorbent core enclosed between the liquid-pervious topsheet and the backsheet.

A suitable topsheet may be manufactured from a wide range of materials such as woven and nonwoven materials (e.g. a nonwoven web of fibers), polymeric materials such as apertured plastic films, e.g. apertured formed thermoplastic films and hydroformed thermoplastic films; porous foams; reticulated foams; reticulated thermoplastic films; and thermoplastic scrims. Suitable woven and nonwoven materials can be comprised of natural fibers (e.g. wood or cotton fibers), synthetic fibers (e.g. polymeric fibers such as polyesters, polypropylene or polyethylene fibers) or from a combination of natural and synthetic fibers. When the topsheet comprises a nonwoven web, the web may be manufactured by a wide number of known techniques. For example, the web may be spun-bonded, carded, wet-laid, melt-blown, hydroentangled, combinations of the above or the like. In accordance with the invention, it is preferred to make use of apertured plastic films (e.g. thermoplastic films) or nonwoven materials based on synthetic fibers, e.g. those made from polyethylene or polypropylene homo- or copolymers and polymer compositions based thereon.

Optionally, at least one further layer exists between the absorbent core and the topsheet and may be made from hydrophobic and hydrophilic web or foam materials. As "web material" we understand coherent flat fiber-based structures of paper tissue, woven or nonwoven type. The nonwoven material may have the same features as described above for topsheets.

Specifically, the at least one further layer may contribute to fluid management, for instance in the form of at least one acquisition/distribution layer. Such structures are taught for instance by U.S. Pat. No. 5,558,655, EP 0 640 330 A1, EP 0 631 768 A1 or WO 95/01147.

"Foam materials" are also well known in the art and for instance describe in EP 0 878 481 A1 or EP 1 217 978 A1 in the name of the present applicant.

The absorbent core may be partially or totally surrounded by a core wrap. It comprises an absorbent material that is generally compressible, conformable, non-irritating to the wearer's skin and capable of absorbing and retaining liquids such as urine and other body exudates.

Examples for absorbent materials include a wide variety of liquid-absorbent materials commonly used in disposable diapers and other absorbent articles such as comminuted wood pulp, which is generally referred to as air felt or fluff, as well as creped cellulose wadding; melt blown polymers, including co-form; chemically stiffened, modified or cross-linked cellulosic fibers; tissue, including tissue wraps and tissue laminates, absorbent foams, absorbent sponges, super-absorbent polymers (such as superabsorbent fibers or particles), absorbent gelling materials, or any other known absorbent materials or combinations of materials.

The fibers typically present in the absorbent core are preferably also capable of absorbing body liquid as is the case for hydrophilic fibers. Most preferably the fibers are cellulosic fibers such as wood pulp fluff, cotton, cotton linters, rayon, cellulose acetate and the like, the use of cellulosic fluff pulp being preferred. The cellulosic fluff pulp can be of mechanical or chemical type, the chemical pulp being preferred.

The absorbent core preferably comprises suberabsorbent polymers and/or cellulosic fluff pulp fibers. If used in admixture, the SAP/fluff pulp weight ratio is preferably 20/80 to 70/30, e.g. 30/70 to 60/40.

The term "superabsorbent polymers" is well known in the art and designates water-swellable, water-insoluble materials capable of absorbing the multiple of their own weight in body fluids. Preferably, the superabsorbent polymer (SAP) is capable of absorbing at least about 10 times its weight, preferably at least about 15 times its weight, in particular at least about 20 times its weight in an aqueous solution containing 0.9 wt.-% of sodium chloride (under usual measuring conditions where the superabsorbent surface is freely accessible to the liquid to be absorbed). To determine the absorption capacity of the superabsorbent polymer, the standard test EDANA WSP 241.2 can be used.

The superabsorbent polymer may be in any form suitable for use in absorbent articles including particles, fibers, flakes, spheres and the like, the particle form being preferred.

According to one embodiment, the superabsorbent polymer in the absorbent core comprises an acidic superabsorbent since acidic components may exert a beneficial influence on odour control. In an alternative embodiment, the absorbent core in the absorbent article does not contain an acidic superabsorbent material, in particular an acidic superabsorbent material having a pH of • 5.5. Thereby, the pH of both standard (i.e. non-acidic) and acidic SAP is measured using the standard test EDANA WSP 200.2.

SAPs are based on homo- or copolymers comprising at least one polymerizable unit having an acidic group (e.g. a carboxylic acid group or a sulfonic acid group) such as methacrylic acid, acrylic acid, maleic acid, vinylsulfonic acid. The corresponding polymers include, but are not limited to poly(meth)acrylic acids, ethylene maleic anhydride copolymers, polymers and copolymers of vinylsulfonic acids, polyacrylates, acrylic acid grafted starch and isobutylene maleic anhydride copolymers. These polymers are preferably crosslinked to render the materials substantially water insoluble. According to one preferred embodiment of the present invention, the superabsorbent material is a crosslinked homo- or copolymer comprising (meth)acrylic acid units, for instance of the type disclosed in EP 0 391 108 A2. Standard SAPs have a pH which lies e.g. in a range of 5.8 or more.

An "anti-bacterial agent" is defined in the present invention as a compound which is able to either kill bacteria, such as ammonia-generating bacteria which exist in the urogenital region of humans, or to suppress the growth of said bacteria.

Preferred anti-bacterial agents are capable of yielding when starting at a concentration of about $10^3$ CFU/ml. liquid for each type of bacteria (CFU is colony-forming unit) and at a given concentration of the anti-bacterial agent (e.g. $10^{-3}$ g/g dry absorbent core) an amount of bacteria after 12 hours of $10^5$ CFU/ml liquid for each type of bacteria or lower, preferably $10^4$-10 and more preferably $10^3$-$10^2$. This can be measured in line with the method "measuring bacteria inhibition in absorbent bodies" as described in WO 00/35505 (page 17, method 3) in the name of the present applicant. The absorbent core used in the above method preferably is circular, has a diameter of 5 cm, the amount of absorbent material present in the core is 1.16 g and the absorbent core has been compressed to a bulk of about 8-10 $cm^3$/g, and to this 16 ml of test liquid is added. This method evaluates the capacity to suppress the growth of or to kill at least one bacterial strain selected from the species *Escherichia coli, Proteus mirabilis* and *Enterococcus faecalis*.

Anti-bacterial agents for use in the present invention are preferably compounds which are skin-friendly. It needs to be borne in mind that the skin area being in contact with absorbent products such as diaper, panty diaper, sanitary napkin or incontinence device is sensitive and delicate. Anti-bacterial agents which are approved for the use in food (e.g. as preservatives) are therefore used with preference (for instance those food preservatives being approved at the priority of the present application in any EC member state or the US or Japan).

The anti-bacterial agent may be organic or inorganic. It may for instance be selected from the following organic compounds: isothiazolinones and benzisothiazolinones, oxazolidines, pyridines, optionally chlorinated phenols, bromo compounds, aldehyde and dialdehyde compounds, benzyl alcohols, cresols, p-hydroxybenzoic acids and their esters and salts (parabene compounds), organic acids and their salts, in particular alkali metal and earth alkaline metal salts and organic polyacids and their salts, in particular alkali metal and earth alkaline metal salts. An anti-bacterial agent belongs to the above classes if it displays (comprises) the corresponding structural features. Accordingly, (further) substituted members such as hydroxylated organic acids are also covered by the above classes.

The inorganic anti-bacterial agent may be selected from sulfites, bisulfites, nitrates, nitrites and iodates of alkali metals such as sodium and potassium or earth alkaline metals such as calcium or magnesium.

Preferably, one of the following compounds or a mixture thereof is used as an anti-bacterial agent.

1,2-benzisothiazoline-3-one (BIT, Proxel);
benzoic acid, E 210;
benzyl alcohol;
2-benzyl-4-chlorophenol (Chlorophene);
1,3-bis(hydroxymethyl)-5,5-dimethylimidazoline-2,4;
5-bromo-5-nitro-1,3-dioxane (Bronidox™);
2-bromo-2-nitropropane-1,3-diol (BNPD);
succinic acid dialdehyde;
dehydroacetic acid (6-methylacetopyranone);
diazolidinyl urea (Germall II™);
1,2-dibromo-2,4-dicyanobutane;
6,6-dibromo-4,4-dichloro-2,2'-methylenediphenol;
3,3'-dibromo-4,4'-hexamethylene dioxydibenzamindine (dibromohexamidine);
2,4-dichlorobenzyl alcohol;
5,5'-dichloro-2,2'-dihydroxydiphenylmethane (Dichlorophen);
4,4-dimethyl-1,3-oxazolidine;
phenols, e.g. o-phenylphenol;
cresols, e.g. o-, m- or p-cresol, 4-isopropyl-m-cresol, p-chloro-m-cresol;
2-phenoxyethanol (ethylene glycol monophenyl ether);
1-phenoxypropane-2-ol;
o-phenylphenol and salts thereof;
phenyl mercury silver salts including borates;
formaldehyde;
fumaric acid, E 297;
glutaraldehyde;
glyoxal;
hexetidine;
hexamethylenetetramine, E 239;
p-hydroxybenzoic acid (4-hydroxybenzoic acid);
p-hydroxybenzoic acid-benzylester (benzyl parabene);
p-hydroxybenzoic acid-n-butylester (butyl parabene);
p-hydroxybenzoic acid-ethylester, E 214 (ethyl parabene);
p-hydroxybenzoic acid-ethylester sodium salt, E 215 (ethylparabene sodium salt);
p-hydroxybenzoic acid-n-heptylester (heptyl parabene);
p-hydroxybenzoic acid-methylester, E 218 (methyl parabene);
p-hydroxybenzoic acid-methylester sodium salt, E 219 (methyl parabene sodium salt);
p-hydroxybenzoic acid-n-propylester, E 216 (propyl parabene);
p-hydroxybenzoic acid-n-propylester sodium salt, E 217 (propyl parabene sodium salt);
1-hydroxy-4-methyl-6(2,4,4-trimethylpentyl)-2-pyridone;
imidazolidinyl urea;
calcium acetate, E 263;
calcium bisulfite, E 227;
calcium propionate, E 282;
calcium sulfite, E 226;
potassium disulfite, E 224 (potassiumpyrosulfite);
potassium nitrate, E 252;
potassium propionate, E 283;
potassium sorbate, E 202;
2-chloracetamide;
N-(3-chloroallyl)-hexaminiumchloride (Quaternium 15);
1-(4-chlorphenoxy)-1-(imidazol-1-yl)-3,3-dimethylbutan-2-one;
Chlorhexidine;
p-chloro-m-xylenole;
5-chloro-2-methyl-4-isothiazoline-3-one;
4-chloro-3,5-xylenole;
metenamine-3-chloroallylchloride;
n,n'-methylenebis(5-methyl-oxazolidine) (Grotan OD™);
2,2'-methylene-bis-(3,4,6-trichlorophenol) (Hexachlorophene);
lactic acid E 270;
myristic acid;
natamycin, E 235 (Pimaricin);
sodium acetate, E 262;
sodium benzoate, E 211;
sodium diacetate, E 262;
sodium forminate, E 237;
sodium nitrate, E 251;
sodium nitrite, E 250;
sodium propionate, E 281;
sodium-2-pyridinethiol-1-oxide (Omadin™ and PyrionNa™);
sodium sorbate, E 201;
sodium sulfite, E 221;
sodium disulfite, E 223 (sodium pyrosulfite);
sodium iodate;
sodium hydrogensulfite, E 222 (sodium bisulfite);
Nisin, E 234;
2-n-octyl-4-isothiazoline-3-one (Kathon 893™ and Skane M-8™);
Paraformaldehyde;
poly(1-hexamethylene biguanide hydrochloride);
propionic acid, E 280;
salicylic acid (2-hydroxybenzoic acid);
sorbic acid, E 200;
inorganic sulfites;
sulfur dioxide (aq.), E 220;
2,2'-thio-bis-(4,6-dichlorophenol) (Bithionol);
Thiomersal (ethyl mercury thiosalicylate);
1,3,5-triazine-1,3,5-(2H, 4H, 6H)-triethanol;
trichlocarban (3,4,4'-trichlorocarbanilide);
2,4,4'-trichloro-2'-hydroxydiphenylether (Irgasan DP300™ and Triclosan™);
3,4,4-trimethyl-1,3-oxazolidine (Bioban CS1135™ and Oxaben A™);
undecene acid;
inorganic hydrogensulfites;
zinc-bis-(2-pyridinethiol-1-oxide) (Zink-Omadin™);
malic acid, E 296 (hydroxy succinic acid);
acetic acid, E 260;
morpholine derivatives, e.g. 4-(nitrobutyl)-morpholine and 4,4'-(2-ethyl-2-nitro-trimethylene)-dimorpholine (Bioban P 1487™ or Bioban CS1248™);
oxazolidines;
pyridine derivatives;
Kathon CG (mixture of 5-chloro-2-methyl-4-isothiazoline-3-one and 2-methyl-4-isothiazoline-3-one); and
1,1,1-trichloro-2-methyl-2-propanol (chlorobutanol).

The anti-bacterial agent is preferably selected from organic acids and polyacids (e.g. diacids or triacids), and their salts. The organic (poly)acid may be substituted by one, two or more hydroxy groups. The organic (poly)acid may be an unsaturated (e.g. mono- or diunsaturated) or saturated, linear or branched aliphatic carboxylic acid preferably having from 2 to 18 carbon atoms, more preferably 3 to 8 carbon atoms. Examples thereof were already mentioned in the above list. The organic acid may also represent an aromatic (poly)acid, preferably a phenyl(poly)carboxy acid, having preferably from 7 to 18 carbon atoms, in particular 7 to 10 carbon atoms as in benzoic acid, p-hydroxybenzoic acid or salicylic acid. The salt is preferably an alkali metal (e.g. K or Na) or earth alkaline metal salt (e.g. Ca or Mg).

Acidic anti-bacterial agents, including the above organic (poly)acids are preferably weak acids, in particular those having a pK value of at least 3, in particular at least 4, e.g. 4 to 5 (for polyacids the pK1 value) measured in water at 25° C. Acetic acid has for instance a pK of 4.75, sorbic acid a pK of 4.76 and benzoic acid a pK of 4.19.

More preferably benzoic acid, sorbic acid, tartaric acid or citric acid, most preferably benzoic acid, are used as the anti-bacterial agent in the present invention.

The alkali metal chloride may be potassium chloride (KCl) or sodium chloride (NaCl) and is preferably NaCl. The alkaline earth metal chloride may be magnesium chloride ($MgCl_2$) or calcium chloride ($CaCl_2$). According to the invention, the alkali metal chloride or alkaline earth metal chloride is present in an amount of at least 0.01, preferably at least 0.05, more preferably at least 0.1 g per g dry absorbent core.

There are no specific restrictions regarding the organic zinc salt to be used in combination with the component (i). In accordance with the present invention, zinc salts of organic carboxylic acids having 2 to 30 carbon atoms, in particular 12 to 24 carbon atoms are preferably used. The carboxylic acid group may be attached to aliphatic, aliphatic-aromatic, aromatic-aliphatic, alicyclic, or aromatic residues, wherein the aliphatic chain or the alicyclic ring(s) may be unsaturated and are optionally substituted, for instance by hydroxy or C1 to C4 alkyl. These salts include zinc acetate, zinc lactate, zinc ricinoleate and zinc abietate. More preferably, the zinc salt is the zinc salt of an unsaturated hydroxylated fatty acid having 8 to 18 carbon atoms. Although there is no specific restriction regarding the number of unsaturated double bonds or hydroxy groups, those fatty acids having one or two unsaturated double bonds and one or two hydroxyl groups seem to be preferred. The most preferred embodiment is zinc ricinoleate. The organic zinc salt may also be activated by the presence of amino acids as in TEGO® Sorb available from Degussa. Further, the organic zinc salt to be used in the present invention may also be capable of removing malodorous substances chemically based on amines, e.g., nicotine in cigarette smoke, thiocompounds, e.g., allicin in garlic and onions, and acids, e.g., isovaleric acid in human sweat, and butyric acid. For instance, zinc ricinoleate which is, e.g., marketed by Degussa under the tradename TEGO® Sorb has the described additional odor removing effect apart from removing ammonia.

According to a particular preferred embodiment, the anti-bacterial agent (as one alternative of component (i)) is selected from the group consisting of benzoic acid, sorbic acid, tartaric acid and citric acid, or a mixture thereof, and the organic zinc salt is zinc ricinoleate. According to still further preferred embodiments, sodium chloride is used as component (i), and the organic zinc salt is zinc ricinoleate.

As regards the amount of component (i) and organic zinc salt to be used in the present invention, there are no specific restrictions. In the present specification, these amounts are expressed in relation to the weight (in g) of the dry absorbent core. Herein the term "dry" used in relation to the absorbent core is to be understood such that no water has been added to the absorbent core and that the only water present in the absorbent core is the unavoidable residual water from manufacturing. For the purpose of the present invention, an absorbent core is preferably regarded as "dry" after a circular test core having a thickness of 5 to 6 mm, a diameter of 5 cm and which has been compressed to a bulk of about 8-10 $cm^3$/g has been kept for at least one week at ambient temperature (e.g. 20° C.) and a specified relative humidity, for example 50% RH.

While there are no specific restrictions as to the amount of anti-bacterial agent to be used in the present invention, as long as the object of the present invention is not compromised, the amount of anti-bacterial agent is preferably at least $1 \times 10^{-4}$ g, more preferably at least $5 \times 10^{-4}$ g, most preferably at least $1 \times 10^{-3}$ g per g of dry absorbent core. However, there are cases where the anti-bacterial agent can be used in amounts as low as 5 to 10 ppm of antibacterial agent(s) (by weight) in terms of the dry absorbent core. Such a case is Kathon® CG, which is a mixture of two compounds, namely 5-chloro-2-methyl-4-isothiazoline-3-one and 2-methyl-4-isothiazoline-3-one, Beyond a certain amount of anti-bacterial agent (for instance 0.01 g or 0.1 g per g dry absorbent core), it may no longer be economical to add further anti-bacterial agent.

The amount of alkali metal chloride or alkaline earth metal chloride, such as sodium chloride is at least 0.01 g, preferably at least 0.05 g, for instance at least 0.1 g per g dry absorbent core. There is no specific upper limit for the (earth) alkali metal chloride content, although it may no longer be beneficial to increase the amount beyond values such as 0.5 g per g absorbent core or 1 g per g absorbent core.

Very low amounts of organic zinc salts cooperate already with component (i) in a very efficient odour control. A preferred lower weight limit of organic zinc salt (calculated as zinc), such as zinc ricinoleate seems to be at least $1 \times 10^{-5}$ g per g of dry absorbent core. More preferred values are at least $1 \times 10^{-4}$ g, even more preferably at least $5 \times 10^{-4}$ g per g dry absorbent core, even more preferably at least $1 \times 10^{-3}$ g per g of dry absorbent core. There is no specific upper limit, even though for economic reasons, a point may be reached where it may no longer be useful to further increase the zinc content, for instance to values of 0.1 or 1 g zinc per g absorbent core, if this is not accompanied by an enhanced odour suppression.

The weight ratio of the anti-bacterial agent, alkali metal chloride or alkaline earth metal chloride, and the organic zinc salt is also not specifically limited, but it is preferably 15/1 to 1/5, more preferably 5/1 to 1/2, for instance 3/1 to 1/1.

The present invention is also not subject to any limitations regarding the technique of incorporating the anti-bacterial agent or alkali metal or alkaline earth metal chloride (in the following also "the chloride") and the organic zinc salt into the absorbent core. However, dipping, impregnation and spraying are preferred.

For instance, it is conceivable to treat the pulp fibers to be used in the absorbent core, preferably cellulosic fluff pulp with a mixed solution of the organic zinc salt prior to or during admixture with the SAP. In the alternative, the fibers to be used in the absorbent core can be treated successively with separate solutions, e.g. by dipping and spraying, a first solution comprising the anti-bacterial agent or the chloride, and a second solution comprising the organic zinc salt.

According to one embodiment, the superabsorber (SAP) to be used in the absorbent core is treated with a mixed solution of the organic zinc salt prior to or during admixture with the pulp fibers, in particular cellulosic fluff pulp. In the alternative, the SAP to be used in the absorbent core can be treated successively with separate solutions, e.g. by dipping and spraying, a first solution comprising the anti-bacterial agent or the chloride, and a second solution comprising the organic zinc salt.

According to another embodiment, a mixed solution of the organic zinc salt and the anti-bacterial agent or chloride is sprayed onto the fibers, most preferably onto the cellulosic fluff pulp sheets as obtained from the manufacturer. The mixed solution can be sprayed onto the fluff pulp sheet directly by the manufacturer of these sheets prior to the delivery of the sheets to the manufacturer of the absorbent articles. This is an especially preferred embodiment since it avoids the extra step of spraying the mixed solution or the separate solutions (i.e. of the organic zinc salt and component (i)) when manufacturing the absorbent article. Alternatively, the pulp sheet is dipped into the solution. The SAP can be added during or after sheet formation to obtain an absorbent core treated in accordance with the present invention.

The most preferred way is to pretreat the SAP or the pulp fibers, in particular the fluff pulp fibers, with a mixed solution or separate solutions of the organic zinc salt and the anti-bacterial agent or chloride and to incorporate these components along with the pulp in the absorbent core during core formation.

According to one preferred application technique, the solution(s) of component(i), in particular benzoic acid, and component(ii), in particular zinc ricinoleate are sprayed on one or both sides of the absorbent core, or one of both sides of the individual layers constituting the same.

The solvent used for the mixed solution of (i) anti-bacterial agent or chloride and (ii) organic zinc salt can be water, a preferably volatile organic solvent such as ethanol or a mixture of water and a water-miscible organic solvent such as ethanol, as long as the components (i) and (ii) will dissolve or can be dispersed therein. Preferably, these solvents are also used when preparing two separate solutions of component (i) and (ii). In the case of the two solutions, the solvents can be selected independently dependent on the solubility of component (i) and the organic zinc salt. Preferably, the components (i) and (ii) are present in the solution(s) in a relatively high concentration, preferably 1 to 30 wt.-%. The use of such concentrated solutions ensures that the absorption capacity of the superabsorbent material is not impaired more than necessary. Commercially available solutions of organic zinc salts such as TEGO® Sorb A30 available from Degussa (content of actives 30 weight %, zinc ricinoleate activated by an amino acid), optionally in a diluted form, to which an appropriate amount of desired compound (i) is added, can also be employed.

The backsheet prevents the exudates absorbed by the absorbent layer and contained within the article from soiling other external articles that may contact the absorbent article, such as bed sheets and undergarments. In preferred embodiments, the backsheet is substantially impervious to liquids (e.g., urine) and comprises a laminate of a nonwoven and a thin plastic film such as a thermoplastic film having a thickness of about 0.012 mm to about 0.051 mm. Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the absorbent article while still preventing exudates from passing through the backsheet. Exemplary breathable materials may include materials such as woven webs, nonwoven webs, composite materials such as film-coated nonwoven webs, and microporous films.

The above elements of an absorbent article can be assembled, optionally together with other typical elements of absorbent articles in a manner known in the art.

The present invention is also concerned with cellulosic fibers, in particular cellulosic fluff pulp fibers comprising components (i) and (ii) as specified above. The cellulosic fibers can be obtained by treating the same in a manner as described above.

The following examples and comparative examples illustrate the present invention without limiting same.

EXAMPLE 1

Circular test absorbent cores having a weight of about 1.48 g and a diameter of 5 cm were punched out of an absorbent core produced in a pilot plant. A standard method of mat forming a core was used in the production of the core in the pilot plant. The absorbent core consisted of a homogenous mixture of fluff pulp, sodium chloride and superabsorbent material. The fluff pulp used was 0.69 g Weyerhauser pulp (NB 416) and the superabsorbent material was 0.47 g of a superabsorber (Dow Chemicals XZ 91030.03). Sodium chloride (NaCl) was used in an amount of 163 g/m$^2$ (corresponding to 0.32 g/g dry absorbent core). The absorbent core was compressed to a bulk of about 8-10 cm$^3$/g.

To the absorbent core, 1.3 ml of a solution containing 0.5 wt % zinc ricinoleate (available from Degussa under the tradename TEGO® Sorb A30 and suitably diluted) was added by either dripping the solution onto the surface (on one side) or dipping one side of the core into the solution. 1 week after the treatment, the absorbent core was allowed to absorb 16 ml synthetic urine according to Method A as described below and then allowed to stand at room temperature.

6 h and 8 h after the absorption of synthetic urine the amount of ammonia developed was measured.

Five measurements were averaged as mean value. The results are shown in Table 1.

Method A: Measurement of Ammonia Inhibition in Absorbent Cores

Absorbent cores were prepared as described above. Test liquid 1 was prepared. Bacteria suspension of *Proteus mirabilis* was cultivated in nutrient broth 30° C. overnight. The graft cultures were diluted and the bacterial count was determined. The final culture contained approximately 10$^5$ bacteria per ml of test liquid. The absorbent core was placed in a plastic jar and the Test liquid 1 was added to the absorbent core, whereafter the container was incubated at 35° C. 6 and 8 hours, respectively, whereafter samples were taken from the containers using a hand pump and a so called Dräger-tube. The ammonia content was obtained as a colour change on a scale graded in ppm or volume percent.

Test Liquid 1:

Sterile synthetic urine to which has been added a growth medium for micro-organisms. The synthetic urine contains mono- and divalent cations and anions and urea and has been prepared in accordance with the information in Geigy, Scientific Tables, Vol 2, 8$^{th}$ ed. 1981 p. 53. The growth medium for the micro-organisms is based on information of Hook- and FSA-media for entero-bacteria. The pH in this mixture is 6.6.

COMPARATIVE EXAMPLE 1

An absorbent core was formed in the same manner as in Example 1, with the exception that not treatment solution was applied to the absorbent core so that it did not contain any zinc ricinoleate.

COMPARATIVE EXAMPLE 2

An absorbent core was formed in the same manner as in Example 1 with the sole difference that the core did not contain any sodium chloride (weight of absorbent core about 1.16 g) and that the solution used for treating the absorbent core contained 6 wt % of zinc ricinoleate, and no sodium chloride.

The results in terms of ammonia formation of Example 1 and Comparative Examples 1 and 2 are shown in the following Table 1.

TABLE 1

| | sample description | Ammonia Formation (ppm) 6 h | Ammonia Formation (ppm) 8 h |
|---|---|---|---|
| CEx 1 | NaCl | 77 | 520 |
| CEx 2 | Zn[1] | <19 | 270 |
| Ex 1 | NaCl + Zn[1] | 10 | 140 |

[1]Zinc ricinoleate

The above experiments show that the combined use of an alkali metal chloride, such as sodium chloride, and an organic zinc salt, such as zinc ricinoleate suppresses the formation of ammonia to a very surprising extent.

The invention claimed is:

1. Absorbent article comprising a topsheet, a backsheet and
   an absorbent core enclosed between said topsheet and said backsheet, wherein said absorbent core comprises
   (i) an anti-bacterial agent or, in an amount of at least 0.01 g per g dry absorbent core, at least one alkali metal or alkaline earth metal chloride, and
   (ii) an organic zinc salt, wherein the amount of organic zinc salt is such that at least $5 \times 10^{-4}$ g Zn per g dry absorbent core is contained in the absorbent core.

2. Absorbent article comprising a topsheet, a backsheet and
   an absorbent core enclosed between said topsheet and said backsheet, wherein said absorbent core comprises
   (i) an anti-bacterial agent or, in an amount of at least 0.01 g per g dry absorbent core, at least one alkali metal or alkaline earth metal chloride, and
   (ii) an organic zinc salt, wherein the absorbent core comprises the anti-bacterial agent, wherein the amount of anti-bacterial agent is at least $1 \times 10^{-3}$ g per g dry absorbent core.

3. Absorbent article comprising a topsheet, a backsheet and an absorbent core enclosed between said topsheet and said backsheet, wherein said absorbent core comprises
   (i) an anti-bacterial agent or, in an amount of at least 0.01 g per g dry absorbent core, at least one alkali metal or alkaline earth metal chloride, and
   (ii) an organic zinc salt, wherein the absorbent core comprises the anti-bacterial agent, wherein the weight ratio of the anti\- bacterial agent and the organic zinc salt, in terms of zinc, is 15/1 to 1/5.

4. Absorbent article comprising a topsheet, a backsheet and an absorbent core enclosed between said topsheet and said backsheet, wherein said absorbent core comprises
   (i) an anti-bacterial agent or, in an amount of at least 0.01 g per g dry absorbent core, at least one alkali metal or alkaline earth metal chloride, and
   (ii) an organic zinc salt, wherein the absorbent core comprises the anti-bacterial agent, wherein the anti-bacterial agent is selected from the group consisting of organic acids and polyacids, and their salts, having 2 to 18 carbon atoms.

5. Absorbent article according to claim 4, wherein the organic acid or polyacid is selected from the group consisting of saturated or unsaturated linear or branched carboxylic acids having from 3 to 8 carbon atoms and aromatic acids and polyacids having from 7 to 10 carbon atoms.

6. Absorbent article according to claim 5, wherein the acid or polyacid is selected from the group consisting of benzoic acid, sorbic acid, tartaric acid, citric acid, and mixtures thereof.

7. Absorbent article according to claim 6, wherein the acid is benzoic acid.

8. Absorbent article comprising a topsheet, a backsheet and an absorbent core enclosed between said topsheet and said backsheet, wherein said absorbent core comprises
   (i) an anti-bacterial agent or, in an amount of at least 0.01 g per g dry absorbent core, at least one alkali metal or alkaline earth metal chloride, and
   (ii) an organic zinc salt, wherein the organic zinc salt is selected from zinc salts of carboxylic acids having 2 to 30 carbon atoms.

9. Absorbent article according to claim 8, wherein the carboxylic acid represents an unsaturated hydroxylated fatty acid having 8 to 18 carbon atoms.

10. Absorbent article according to claim 9, wherein the zinc salt is zinc ricinoleate.

11. Absorbent article comprising a topsheet, a backsheet and
    an absorbent core enclosed between said topsheet and said backsheet, wherein said absorbent core comprises
    (i) an anti-bacterial agent or, in an amount of at least 0.01 g per g dry absorbent core, at least one alkali metal or alkaline earth metal chloride, and
    (ii) an organic zinc salt, wherein the absorbent core comprises the anti-bacterial agent, wherein the anti-bacterial agent is benzoic acid and the zinc salt is zinc ricinoleate.

* * * * *